United States Patent
Nagolkin et al.

(10) Patent No.: US 9,878,064 B2
(45) Date of Patent: Jan. 30, 2018

(54) AIR DISINFECTION METHOD AND A DEVICE FOR IMPLEMENTATION THEREOF

(71) Applicants: Alexandr Vladimirovich Nagolkin, Moscow (RU); Elena Vladimirovna Volodina, Moscow (RU)

(72) Inventors: Alexandr Vladimirovich Nagolkin, Moscow (RU); Elena Vladimirovna Volodina, Moscow (RU)

(*) Notice: Subject to any disclaimer, the term of this patent is extended or adjusted under 35 U.S.C. 154(b) by 183 days.

(21) Appl. No.: 14/815,142

(22) Filed: Jul. 31, 2015

(65) Prior Publication Data
US 2017/0028094 A1    Feb. 2, 2017

(51) Int. Cl.
*A61L 9/22* (2006.01)
*F24F 3/16* (2006.01)
*B03C 3/00* (2006.01)

(52) U.S. Cl.
CPC ...................................... *A61L 9/22* (2013.01)

(58) Field of Classification Search
CPC ........................................................ A61L 9/22
(Continued)

(56) References Cited

U.S. PATENT DOCUMENTS

| 5,474,600 A | 12/1995 | Volodina et al. |
| 2002/0063537 A1* | 5/2002 | Nam .......................... A61L 9/22 |
| | | 315/169.4 |

(Continued)

FOREIGN PATENT DOCUMENTS

| RU | 2026751 | 1/1995 |
| RU | 2344882 | 1/2009 |

OTHER PUBLICATIONS

English abstract of RU 2026751.
English abstract of RU 2344882.

*Primary Examiner* — Kevin Joyner
*Assistant Examiner* — Holly M Mull
(74) *Attorney, Agent, or Firm* — Ladas & Parry LLP

(57) ABSTRACT

The invention relates to methods for air disinfection of microorganisms and biological agents by the method of their inactivation by electrostatic fields and filtering by the method of electrostatic precipitation. The method comprises the steps of creating a flow (A) of air to be disinfected; subjecting said flow to constant with electrostatic fields alternating in direction of intensity vector, said electrostatic fields being sequentially arranged along the flow, and created by transversely spaced air permeable electrodes (1); and filtering the treated flow with an electrostatic filter. Electrostatic field concentrators in the form of projections (3) are located on the surface of the electrodes (1), in particular nanoscale projections, and the intensity of each of the alternating electrostatic fields between the electrodes is selected in accordance with the condition of electroporation of microorganism cells or their inactivation. A device for implementing this method is also claimed. The use of the invention provides a fast, effective, and reliable cleaning of air from any kind of microorganisms and viruses, as well as the aerosol particles having size of 0.08 μm. The invention also provides improved hygienic safety due to microorganism inactivation before the filtration step, and because of the absence of dangerous concentrations of ozone and other harmful substances.

9 Claims, 2 Drawing Sheets

(58) Field of Classification Search
USPC .............................................................. 422/4
See application file for complete search history.

(56) References Cited

U.S. PATENT DOCUMENTS

| | | | |
|---|---|---|---|
| 2008/0170971 A1* | 7/2008 | Bergeron | A61L 9/205 422/171 |
| 2011/0209621 A1* | 9/2011 | Volodin | A61L 9/22 96/79 |
| 2013/0202766 A1* | 8/2013 | Rubinsky | A23L 3/32 426/590 |

* cited by examiner

AIR DISINFECTION METHOD AND A DEVICE FOR IMPLEMENTATION THEREOF

TECHNICAL FIELD

The invention relates to the field of disinfection and purification of air of microorganisms and aerosols, namely to methods of air disinfection of microorganisms and biological agents by their permanent inactivation by impact of electrostatic fields and filtration by electrostatic precipitation.

The invention can be used for disinfection and purification of air in combined extract-and-input ventilation systems of <<biologically clean>> areas in medicine, pharmaceutical, microbiological, and food industry and other areas where it is required to ensure infectious and sanitary-epidemiological safety of air. Furthermore, the invention can be used for disinfection of air in transport means including passenger transportation by road and rail, air transportation, space manned flying machines, waterborne and underwater means, etc., as well in personal protective equipment (bioprotective and of anti-aerosol masks, etc.), in autonomous recycling facilities and other equipment.

BACKGROUND ART

A device for sterilizing gas and fine filtration is disclosed in RU 2026751. Said device realizes the method of inactivation of microorganisms comprising inactivation of microorganisms in the air flow, wherein they first are charged by ions of the same or different signs, and then said microorganisms are retained on the electrostatic filter, where they eventually are inactivated. Two ionizers of different polarities can of used in the devices for enhancing the sterilization effect.

However, in such devices the inactivation of microorganisms is carried out only after their retention in the electrostatic filter, which is undesirable as during operation constant accumulation of living microorganisms occurs, and the risk of <<multiple>> ejection from the device in the environment increases.

Furthermore, for inactivation of microorganisms, it is necessary to create high concentration of ions within each said device, which is always accompanied by emission of a significant amount of ozone and nitrogen oxides. Discharge of said gases in the air in high concentrations is dangerous for humans and animals. At the same time, the effectiveness of the inactivation depends on the concentration of ions and ozone within the apparatus, which limits the reliability of operation of such apparatuses.

An apparatus for inactivation and fine filtration of viruses and microorganisms in the air stream is disclosed in RU 2344882. Said apparatus comprises a high voltage power source; a sequentially arranged downstream the air flow means for preliminary treating the air flow, the means being formed of oppositely charged conductive filter elements, between which a dielectric plate of a highly porous permeable material is located; a two-section inactivation chamber, each section comprising coaxially arranged a needle corona electrode and a cylindrical non-corona electrode, each of which is electrically connected to a corresponding conductive filter plate, and a precipitator made of parallel oppositely charged plates of highly porous permeable conductive material, between which plates of permeable highly porous dielectric plates are placed. At least a first downstream conductive filter element of the preliminary treatment means is configured as a cylindrical electrode with a base in the form of a conductive plate made of a porous permeable conductive material adjacent to a plate of a permeable highly porous dielectric material and a plate of highly porous conductive material arranged at a distance from the free end of the cylindrical electrode, said plate being adjacent to the electrically connected needle electrode arranged coaxially to the cylindrical electrode and having its point directed towards the dielectric plate, wherein the cylindrical and needle electrodes are connected to opposite poles of the power supply. In the apparatus, porous permeable electrodes having a three-dimensional structure are used, such as open-cell structure of the bulk material (foamed metal).

During operations of the apparatus, a required concentration of ions of corresponding signs is obtained. In the preliminary treatment means, bioaerosols are charged, and the electric fields of different intensity and gradient act on them. <<Cold plasma>> makes an impact on microorganisms at the points of the needle corona electrodes.

In said apparatus first rough filtering of air from large particles is performed. Then, microorganisms and viruses are charged by the ions of one sign, then by the ions of the opposite sign.

After the preliminary treatment means, the air flow enters the two-section chamber inactivation equipped with two single-ended or the discharge electrodes of different polarities.

In a two-section inactivation chamber multiple recharging of bioaerosol takes place under the action of ions, due to electrical contact with the electrodes of different polarity and the surface of the polarized dielectric filter material. After passing through the inactivation chamber, existing microorganisms and viruses in the air flow will be in the inactivated state.

After passing the inactivation cameras, the particles get sufficient for precipitation charge, and they are retained in the electrostatic precipitator.

The prior art apparatus and the method implemented by said apparatus allow overcoming the disadvantages inherent in the described above apparatus according to RU 2026751. However, the process of inactivation of microorganisms and viruses requires simultaneous provision of many conditions: simultaneously creating a high concentration of ions of the same or different polarity, ozone, intensity of electrostatic fields, and polarization of the dielectric. Simultaneous provision of said conditions and ensuring high efficiency of the inactivation of microorganisms in the apparatus is technically difficult because each of these factors affects the result of the processing. The efficiency of inactivation of microorganisms in such apparatus depends on the concentration of ions and ozone within the apparatus, dielectric properties, intensity of the electric fields between the electrodes, and other characteristics. It greatly affects the reliability of the apparatus. Furthermore, for decomposition of ozone in such apparatus requires use of a catalysts, which require constant monitoring of their performance, thereby limiting the safe use of this apparatus in premises with people, and requires additional measurements to ensure operation safety.

The main purpose of the invention is to improve the efficiency of air disinfection by using for rapid inactivation of a microorganism cell electroporation in electrostatic fields followed by filtration of inactivated microorganisms and particulate matter in an electrostatic precipitator.

Further objects of the present invention are to reduce the discharge of ozone and other harmful substances in the process of air disinfection, and to improve reliability of the apparatus.

SUMMARY OF INVENTION

Said problems are solved by the claimed air disinfection method, which includes the steps of: providing a air flow to be disinfected; subjecting said flow to the action of electrostatic fields being arranged successively along the flow, said fields alternating in the direction of the intensity vector are created by transversely positioned electrodes permeable to air; and filtering the treated air flow by an electrostatic filter. According to the invention, there are electrostatic field concentrators in the form of projections with the base diameter not exceeding 30 μm are formed on the surface of the electrodes, and the intensity of each of the alternating electrostatic fields between the corresponding electrodes is selected in accordance with the condition of electroporation of microorganism cells or their inactivation.

As a result of exposure of a microorganism cell to electrostatic fields directed in opposite directions and their high local intensity near the electric field concentrators the magnitudes and polarity of electric potentials on the surface and inside the cell repeatedly changes, whereby there is a change in cell structure, its mechanical and electrical properties, electroporation of cells of microorganisms (formation of pores in the cell membrane) and the subsequent disintegration (distraction) of the structure.

Preferably, the intensity of each of the alternating electrostatic fields between the electrodes is at least 2 kV/cm.

It is desirable to have nanoscaled protrusions with a base diameter of less than 100 nm.

The air flow permeable electrodes are in the shape of plates of porous electrically conductive material or bulk porous fibrous structures.

Preferably, highly porous dielectric plates are arranged between the electrodes. Nanosized projections can also be formed on the surfaces of said plates.

The air flow rate is selected so that the exposure time of each of the permanent alternating electric fields on the particles moving in the air flow to be disinfected is not less than 0.05 seconds.

Preferably, several zones with a high concentration of ions are additionally arranged along the air flow.

The presence of zones with a high concentration of the ions allows charging the aerosol particles by positive and/or negative ions, which enhances the effect of precipitation of these particles.

The zones with a high concentration of ions are preferably formed by performing a corona discharge.

In a part of these zones, there is high concentration of ions of ne polarity, and in the rest zones, the ions are of the other polarity.

Furthermore, the zones with high concentration of ions can be arranged along the air flow before the impact on the air flow by electrostatic fields and/or between the electrodes creating the fields.

The above problems are also solved by an apparatus for disinfecting the air flow comprising the sequentially arranged along the air flow electrodes in the form of permeable for air flow conductive plates arranged across the flow, and a high voltage power source connected to the electrodes so that electrodes have alternating polarity. According to the invention, the electrodes are on the surface of the electric field concentrator in the form of projections, the base diameter not exceeding 30 μm.

The concentrators of electrostatic field on the electrodes provide the appearance of local zones of high intensity, and the alternation of these local zones, the zones of low intensity and the zones without intensity of the electrostatic fields when the direction and magnitude of the intensity of these fields change, leads to rapid electroporation of microorganism cells and disintegration of their structure.

Preferably, the projections are nanosized with a base diameter of not more than 100 nm.

Conductive plates permeable for the air flow and made of a porous electrically conductive material or bulk porous fibrous conductive structures can be additionally provided.

Highly porous dielectric plates also having nanosized projections on their surfaces can be additionally arranged between the electrodes.

At least one zone with a high concentration of ions can be formed between the electrodes.

If several zones of a high concentration of ions are formed between the electrodes, the ions of said zones of high concentration are of the same polarity, and the ions of in other zones are of the other polarity.

Preferably, the zones with a higher concentration of ions of the same polarity alternate with zones of high concentration of ions of the opposite polarity.

In addition, before the first electrode downstream the air flow, at least one zone of a high concentration of ions is fouled. If there are several such zones, it is preferable that the ions in these zones are of the same polarity.

All the above zones of high concentration of ions can be formed by performed as a needle corona electrode arranged coaxially with a non-corona cylindrical electrode.

Preferably, at least one zone of a higher concentration of ions is limited at the inlet by a highly porous permeable electrode of polarity coinciding with the polarity of the nearest electrode, wherein at the outlet said zone can also be limited by a highly porous permeable electrode of polarity coinciding with the polarity of the nearest electrode.

BRIEF DESCRIPTION OF DRAWINGS

The foregoing and other features and aspects of the invention will be best understood with reference to the following description of certain exemplary embodiments of the invention, when read in conjunction with the accompanying drawings, wherein.

Implementation of the method according to the invention is illustrated by the embodiment of the apparatus schematically shown in the Figures.

Figure 1:
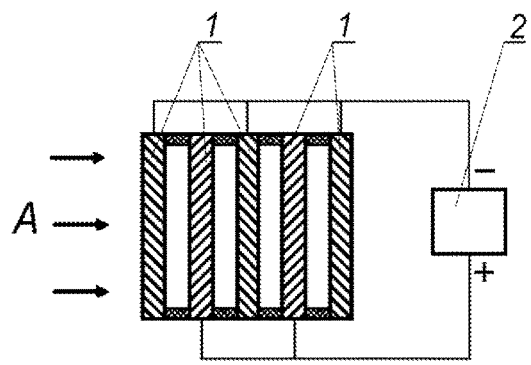
FIG. 1 is a cross-sectional schematic view of an apparatus for disinfecting air according to the invention.

FIG. 1 shows the simplest embodiment of an apparatus implementing the method according to the invention.

BEST MODE FOR CARRYING OUT THE INVENTION

Figures 7, 8:
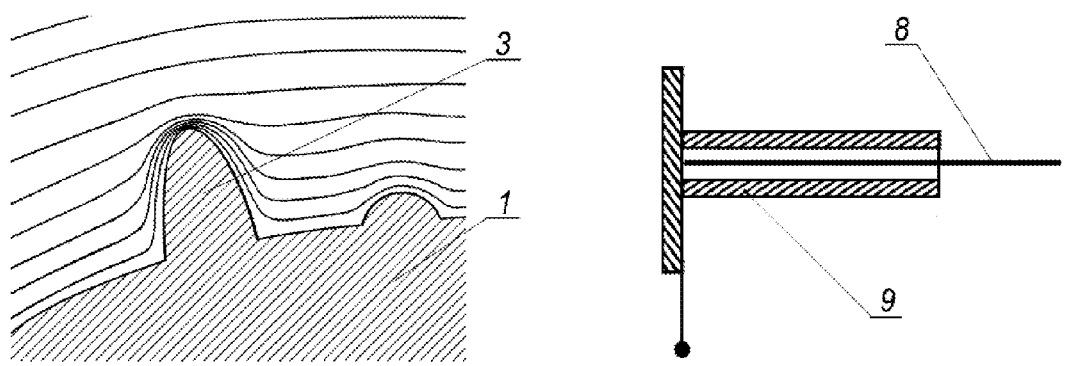
FIG. 7 is a diagram of changes of the electrostatic field intensity near the nanoscaled projections on an electrode.
FIG. 8 is a cross-sectional view of an embodiment of a needle corona electrode.

The apparatus comprises electrodes 1 arranged sequentially along the air flow A of 1 in the form of permeable to air flow conductive plates located across the flow, and a high voltage power source 2 connected to the electrodes 1 so that the electrodes 1 have alternating polarity. The plates of electrodes 1 can be made of various materials: permeable foam metals, porous electrically conductive powder materials, bulk fibrous porous structures, and the like. It is only required to have in the plates of such electrodes an average pore size of not more than 6 mm. On the surface of the electrodes, there are electrostatic field concentrators in the form of projections 3 (FIG. 7), with a base diameter not exceeding 30 μm. Preferably, the projections 3 are nanosized with a base diameter of not more than 100 nm. The nanosized projections 3 on the surface of the electrode 1 can be obtained, e.g., by powder metallurgy techniques. The power supply 2 is selected on the conditions of creating electrostatic field of intensity not less than 2 kV/cm between the adjacent electrodes 1. In this case, near the nanosized protrusions 3, the diameter of which does not exceed the above value, the intensity of the electrostatic field reaches 100 kV/cm or more. As studies have shown, that causes an electrical breakdown of the microbial cell membrane. For creating the required potential difference between the electrodes and the reliability and stability of the apparatus operations, the high voltage power supply must ensure the stabilization of voltage or current.

In operation of the apparatus, an air flow containing microorganisms and aerosol particles passes through the highly porous electrode 1 having on its surface electrostatic field concentrators in the form of protrusions 3. Near the surface of the electrodes, a local high intensity electrostatic field exceeding 100 kV/cm is created due to the projections 3.

Figure 2:
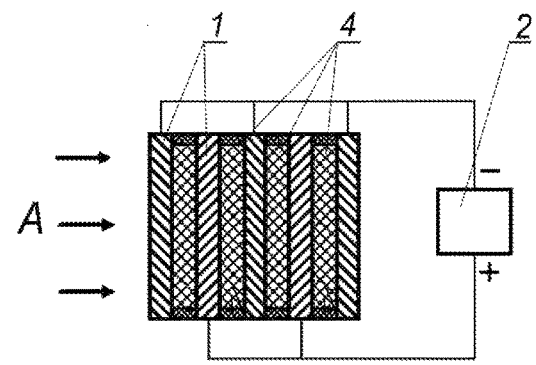
FIG. 2 is the same view, but with a highly porous dielectric plates between the electrodes.

The passage of microorganisms through electrostatic fields repeatedly alternating in direction and magnitude leads to multiple changes in the magnitude and polarity of the electric potentials on the surface and within the cell resulting in changes of cell structure and its electrical and mechanical properties. As a result of repeated depolarization of the cell, in its membrane pores (electroporation) are formed, and its structure disintegrates (is destructed). Inactivation of microorganisms by disrupting their structure eliminates any possibility of adaptations to such impacts, mutations or restoration (<<revival>>), i.e., the inactivation is irreversible. The number of electrodes 1 with projections 3 and the number of direction changes of the electrostatic fields is determined based on the processing air flow rate and the parameters of the processed air. The time required to inactivate all microorganism species can be about 0.5 seconds. Inactivated microorganisms and particulate matter are trapped by the electrostatic filter (not shown). The highly porous dielectric plates 4 can be arranged between the electrodes (FIG. 2) for preventing an electrical breakdown between the electrodes 1 when changing the air or gaseous medium (moisture, dust, temperature, etc.), equalizing the air flow rate in the cross section of the apparatus, and retaining aerosol particles on the surface.

Figure 3:
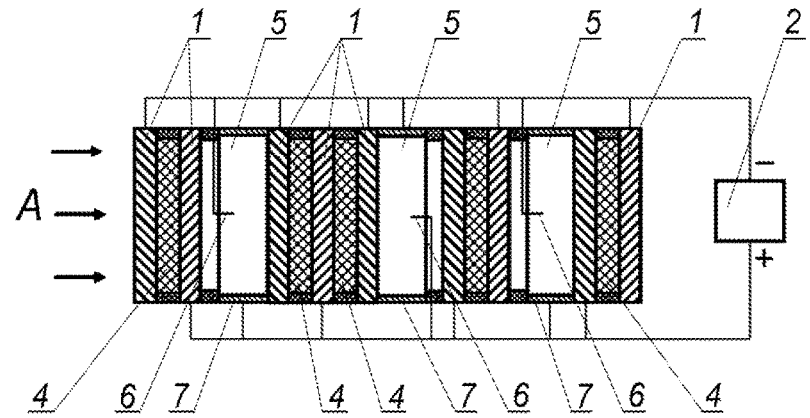
FIG. 3 is the same view as in FIG. 2 but with zones of a higher concentration of ions formed between the electrodes.

The device can be equipped with one or more ionization cameras 5 (FIG. 3) for creating zones with a high concentration of ions to improve the efficiency of the apparatus in high humidity. The electrical parameters of the ionization chambers are chosen such that emission of ozone and nitrogen oxides do not exceed their normalized values. The ionization chamber 5 can be formed as coaxially arranged a needle corona electrode 6 and a cylindrical non-corona electrode 7. In particular, the corona electrode is a needle, such as a wire 8 (FIG. 8) mounted in a metal pipe 9 coaxially thereto and projecting therefrom on an amount sufficient to produce an electrical corona. FIG. 3 shows three ionization chambers 5, wherein in the first and the last chambers downstream the flow the corona electrode is connected to one pole of the power supply 2, and the middle chamber is connected to the other pole, so that the zone with a higher concentration of ions of one plate alternate with the zones of increased concentration of ions of the opposite polarity. However, if there are several ionization chambers in the apparatus, these chambers may be located arbitrarily, without requiring interleaving zones with a high concentration of ions of opposite polarity (not shown). For efficient filtration without increasing emission of ozone, the ionization chambers, for example, can generate ions of the same polarity.

For creating the best conditions for operations of the apparatus comprising the ionization chambers, the power source is configured so that the electrodes 1 are supplied with a constant in value voltage, and the ionization chambers are supplied with stabilized current.

Figure 4:
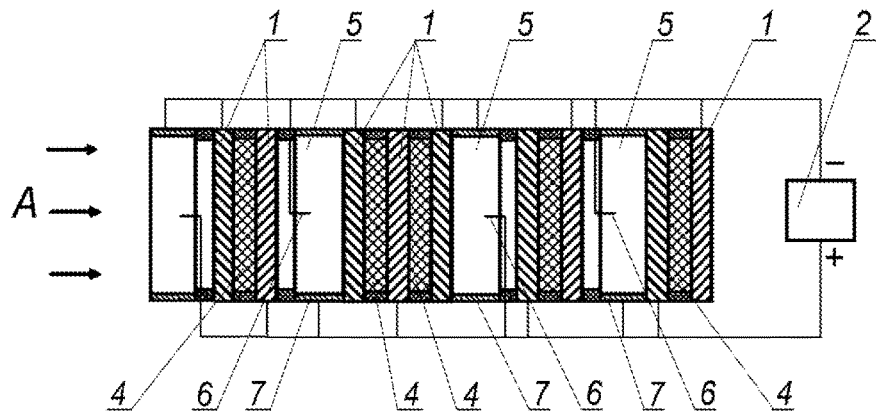
FIG. 4 is same view as in FIG. 3, but with the zone of a high concentration of ions formed before the first electrode downstream of the air flow.

For increasing the intensity of exposure to the aerosol particles and improving the stability of the apparatus in high humidity and dust in the air, is desirable to pre-charge these particles with positive and/or negative ions. For this purpose, at least one zone with a high concentration of ions (FIG. 4) is formed before the first downstream electrode 1 as an ionization chamber 10 similar to any of the ionization chambers 5 located between the electrodes 1.

Figure 5:
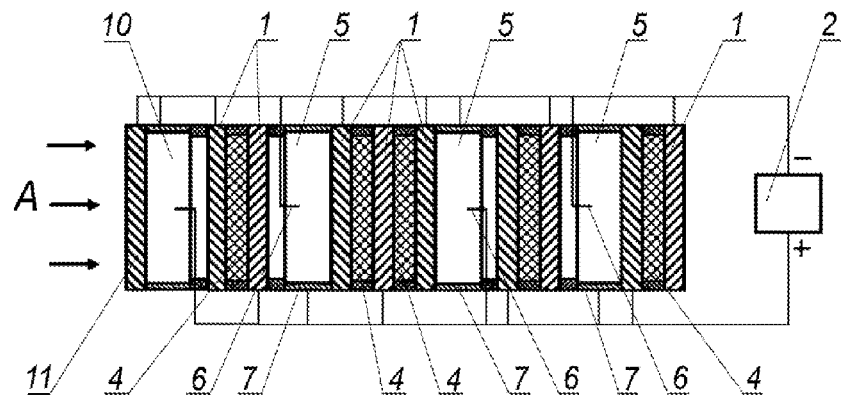
FIG. 5 is the same view as in FIG. 4, but with the highly porous permeable electrode at the inlet to the zone with a high concentration of ions formed before the first electrode downstream of the air flow.
Figure 6:
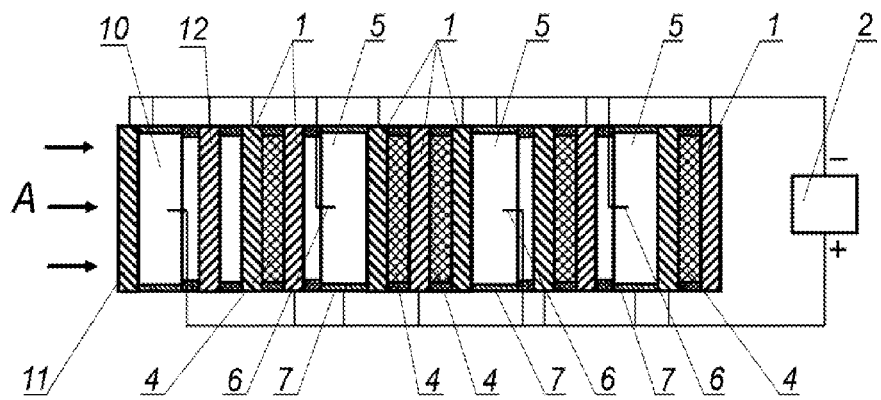
FIG. 6 is the same view as in FIG. 5, but with a highly porous permeable electrode at the outlet of the zone with a high concentration of ions formed before the first electrode downstream the air flow.

The ionization chamber 10 can be limited at the input by a highly porous permeable electrode 11 (FIG. 5), whose polarity coincides with the polarity of the nearest electrode 1. A highly porous permeable electrode 12 (FIG. 6) can also be disposed at the output of the ionization chamber 10, the polarity of which coincides with the polarity of the nearest electrode 1.

Limitation of the ionization chamber 10 at the inlet and/or outlet with the highly porous permeable electrodes 11 and/or 12 improves the conditions of charging aerosols inside the chamber and facilitates the implementation of multiple recharging the bioaerosol when passing through the apparatus.

For increasing the amount of the preliminary charge of aerosol particles by positive and/or negative ions of the ionization chambers 10 disposed in front of the first downstream electrode, there can be a few such chambers (not shown).

Monitoring the effectiveness of air disinfection can be carried out by monitoring the electrical parameters of the apparatus elements currents, voltages, etc.).

The use of the invention provides a fast, effective, and reliable cleaning of air from of any kind of microorganisms and viruses, as well as the aerosol particles having size of 0.08 μm or more. At the same time, the invention also provides hygienic safety due to inactivation of microorganisms before the filtration step, and because of the absence of dangerous concentrations of ozone and other harmful substances.

If necessary, the purification of air from harmful and unpleasant smelling substances, one or more plates of highly porous electrodes or the plates of highly porous dielectric can have adsorption-catalytic coating.

If it is required to increase the efficiency of the filtration of aerosol particles, additional filter material or a high efficiency filter can be installed between the electrodes of the apparatus.

The invention claimed is:

1. An air disinfection method for the electroporation and inactivation of microorganism cells comprising the steps of:
   (a) providing a flow of air to be disinfected;
   (b) subjecting said flow to treatment by a plurality of electrostatic fields arranged successively along the flow, said fields having respective intensity vectors that alternate in direction with an intensity of a first of said plurality of electrostatic fields being directed in a first direction and an intensity of a second of said plurality of electrostatic fields being directed in an opposite direction and with the first and second plurality of electrostatic fields being transversely positioned permeable to a plurality of air flow electrodes; and then and only then
   (c) filtering the treated air flow through an electrostatic filter, wherein each of the plurality of electrodes has a surface comprising a plurality of electrostatic field concentrators in the form of a plurality of projections with each of the plurality of projections having a base diameter not exceeding 100 nm, wherein a local intensity of each of the alternating electrostatic fields near the electrostatic field concentrators is at least 2 kV/cm, and wherein the local intensity of each of the alternating electrostatic fields together with the alternating direction in intensity of the respective alternating electrostatic fields are such as to cause a magnitude and polarity of electric potentials on surfaces and inside of the microorganism cells present in the air flow to change a plurality of times resulting in the electroporation and inactivation of the microorganism cells without the need to filter the air prior to step (a), the microorganism cells being inactivated prior to being filtered.

2. The method according to claim 1, characterized in that the air permeable electrodes are configured in the form of plates of electrically conductive porous material or of bulk porous fibrous structures.

3. The method according to claim 1, characterized in that air permeable highly porous dielectric plates are arranged between the electrodes.

4. The method according to claim 3, characterized in that nanosized projections are arranged on the surfaces of the highly porous dielectric plates.

5. The method according to claim 1, characterized in that the air flow rate is selected so that the time of exposure of the particles moving in the air flow to be disinfected for each of the alternating electrostatic fields is not less than 0.05 second.

6. The method according to claim 1, characterized in that additionally several zones with a high concentration of ions are arranged along the air flow.

7. The method according to claim 6, characterized in that the zones with a high concentration of ions are created by obtaining a corona discharge.

8. The method according to claim 6, characterized in that in a portion of said zones high concentration of ions of one polarity is produced, and in other zones high concentration of ions of opposite polarity is produced.

9. The method according to claim 6, characterized in that the zones with high concentrations of ions are upstream of treating the air flow with electrostatic fields and/or between said fields.

* * * * *